United States Patent [19]

McConnaughey et al.

[11] Patent Number: 4,489,164
[45] Date of Patent: Dec. 18, 1984

[54] COLORIMETRIC METHOD FOR DETECTING ALDEHYDES IN AIR

[75] Inventors: Paul W. McConnaughey; Elmer S. McKee, both of Pittsburgh, Pa.

[73] Assignee: Mine Safety Appliances Company, Pittsburgh, Pa.

[21] Appl. No.: 412,672

[22] Filed: Aug. 30, 1982

[51] Int. Cl.³ .............................................. G01N 21/78
[52] U.S. Cl. ..................................... 436/130; 422/59; 422/86; 422/88; 436/128; 436/167
[58] Field of Search ...................................... 422/55–56, 422/58–60, 86, 88; 436/130, 128, 169, 170, 167, 168

[56] References Cited

U.S. PATENT DOCUMENTS 4,272,479  6/1981  Huneke et al. ......................... 422/57
4,329,153  5/1982  Leichnitz ............................... 422/86

FOREIGN PATENT DOCUMENTS 2038477  7/1980  United Kingdom ................. 422/60

OTHER PUBLICATIONS

Leichnitz Detector Tube Handbook 8, 1979 pp. 80–81.
Meckbach Chemical Abstracts vol. 45 #4059i.
Huang et al., Chemical Abstracts vol. 51, #1651a.
Huang et al., Chemical Abstracts vol. 53 #15627d.

*Primary Examiner*—Barry S. Richman
*Assistant Examiner*—Michael S. Gzybowski

[57] ABSTRACT

A transparent glass detection tube contains a bed of silica gel which has been impregnated with sulfuric acid. One end of the tube is open to the outside air while the other end is connected to a sampling pump. Outside air is drawn through the tube and aldehydes and moisture in the air are separated and adsorbed on sequential lengthwise portions of the gel bed. At the end of the sampling period, xylene vapors are drawn through the silica gel forming a brownish tint stain on that portion of the bed that has adsorbed aldehydes. The length of the stain is a measure of the amount of aldehydes present in the air sample, i.e. the dosage exposure to aldehydes during the sampling period.

3 Claims, No Drawings

COLORIMETRIC METHOD FOR DETECTING ALDEHYDES IN AIR

FIELD OF THE INVENTION

This invention relates to a colorimetric method (stain-length) for quantitatively determining aldehydes present in air and more particularly to a method that is not sensitive to atmospheric moisture and can be used over long sampling periods, suitably over a work shift or longer.

DESCRIPTION OF PRIOR ART

In the conventional method for determining the concentration of formaldehyde in air, sampled air and xylene vapors are drawn simultaneously through a transparent glass tube which contains an elongate bed of silica gel impregnated with sulfuric acid. The air is drawn through the tube by using a sampling pump. The formaldehyde and xylene react with the silica gel compound to form a very light brown stain on the gel. The length of the brown stain is a measure of the concentration of formaldehyde in the air sample. The conventional method can be used to determine the presence of aldehydes other than formaldehyde and aromatic hydrocarbons other than xylene that react to form colored quinoid compounds, for example, benzene, toluene or monochlorobenzene, can be used as reaction agents.

Over long sampling periods, however, water vapor in the ambient air can cause the stain to fade and eventually become obliterated in as little as four hours at ordinary conditions of relative humidity. Thus the conventional method is not suitable for measuring the "8 hour time weighted average" used by OSHA to define the permissable exposure limits to toxic gases, because such measurement requires sampling over an 8 hour period. Currently, long term aldehyde sampling is accomplished by taking samples of the air during the test period and then performing a chemical analysis of each sample to determine the amount of aldehyde present in the air. At present there is no method to determine aldehydes directly by color development over long air sampling periods.

SUMMARY OF THE INVENTION

It is the object of this invention to provide a colorimetric method of determining aldehydes present in the air that is not adversely affected by atmospheric moisture. Other objectives and advantages will be apparent from the description and the claims.

In accordance with this invention, air to be sampled is passed through a detector tube having an elongate bed of silica gel impregnated with sulfuric acid. Atmospheric moisture and any aldehydes in the sample are separated and adsorbed on sequential lengthwise portions of the bed, by a chromatographiclike separation. The bed is then contacted with an aromatic hydrocarbon vapor capable of reacting with the adsorbed aldehyde to form a colored quinoid compound, whereby the bed is colored over that portion containing adsorbed aldehyde. The length of the colored bed portion is a measure of the aldehyde in the sample and can be compared to a calibrated scale to directly indicate a time weighted average concentration of aldehydes. The method is particularly suitable for the determination of formaldehyde.

DETAILED DESCRIPTION

The following example is illustrative of the invention and the best mode of practicing the invention.

EXAMPLE 1

A transparent tube having an inside diameter of approximately 3 mm. is partially filled with a bed of dried silica gel between 30 and 50 mesh size that has been impregnated with sulfuric acid in the proportions of 20 cc of concentrated sulfuric acid and 10 cc of 30% fuming sulfuric acid per 100 g of silica gel. The bed is 50–70 mm long and held within the tube by porous plugs of glass wool. Detector tubes are conventionally made sealed for storage with suitable score lines to facilitate breaking off the ends of the tube for use.

In the test reported in Table 1, one end of an opened tube was connected to a sampling pump which drew sample air through the tube at a flow rate of 20 cc/minute. The sample air was ordinary room air of approximately 50% relative humidity to which formaldehyde was added in the indicated concentration. Tests were performed at various levels of formaldehyde concentrations for various lengths of time, each listed test reporting the average of four replications. As the sample was drawn through, water vapor was adsorbed on the bed of silica gel and formed a white water stain. The formaldehyde was adsorbed on the bed downstream from the downstream end of the water stain. At the end of the sampling period, a flexible vial containing a glass ampoule of xylene, dissolved in mineral oil to reduce its volatility, was attached to the end of the detection tube opposite the pump. The xylene or other hydrocarbon reactant can be used without dilution. The glass ampoule was broken freeing xylene vapor that is drawn through the detection tube by the sampling pump. The xylene reacted with the formaldehyde present on the bed of silica gel and formed a stain ranging in color from pink to brown over the portion of bed on which the formaldehyde was adsorbed. The length of the stain is a measure of the formaldehyde present in the sample, as illustrated in Table 1. The water stain appears lengthwise from the sample inlet end of the bed and is not used for analyses; the formaldehyde stain appears just downstream of the water stain.

TABLE 1

| Test | Formaldehyde (ppm-In Room Air) | Water Stain (Length in mm) | Brown Stain (Length in mm) | Sampling Time |
|---|---|---|---|---|
| 1 | 1 | 32 | 6 | 5 hours |
| 2 | 2 | 7 | 1.5 | 1.5 hours |
| 3 | 2 | 15 | 4 | 3.5 hours |
| 4 | 2 | 27 | 8 | 8 hours |
| 5 | 3 | 35 | 10 | 5 hours |
| 6 | 3 | 18 | 12 | 8 hours |
| 7 | 5 | 19 | 16 | 8 hours |

As a comparison, when sample air and xylene vapor were passed through identical tubes, in accordance with the conventional method of determining formaldehyde, the stain faded and had completely disappeared after about four hours.

EXAMPLE II

The method of the invention is also suitable for determining aldehydes with substantially instantaneous sampling. In tests using the same tubes and color development as in Example I, air was drawn through the tube by use of a piston type pump at a flow rate of approximately 100 cc/minute. The results of three such tests are reported in Table 2.

TABLE 2

| Test | Relative Humidity of Sample Air | Formaldehyde (ppm-In Room Air) | Water Stain (Length in mm) | Brown Stain (Length in mm) | Pump Strokes |
|---|---|---|---|---|---|
| 1 | 15% | 1 | 2 | 5 | 5 |
| 2 | 50% | 1 | 3.5 | 7 | 5 |
| 3 | 80% | 1 | 4 | 8 | 5 |

It will be recognized by those skilled in the art that the method of this invention is not limited to the exemplified embodiments but can be used with other known color developing reactions of aldehydes and aromatic hydrocarbons.

We claim:

1. A method of determining the time weighted average concentration of an aldehyde in air comprising passing air to be sampled through a transparent tube containing an elongate bed of silica gel impregnated with sulfuric acid, whereby moisture and aldehyde are adsorbed on sequential lengthwise portions of the bed, and then contacting the bed with an aromatic hydrocarbon vapor reactive with the adsorbed aldehyde to form a colored reaction product, whereby a lengthwise portion of the bed will be colored.

2. A method according to claim 1 in which the aldehyde is formaldehyde.

3. A method according to claim 2 in which the hydrocarbon is xylene.

* * * * *